US010905368B2

(12) United States Patent
Franco

(10) Patent No.: US 10,905,368 B2
(45) Date of Patent: Feb. 2, 2021

(54) BEDWETTING TRAINING DEVICE AND METHOD

(71) Applicant: GOGO Band, Inc., Ashland, VA (US)

(72) Inventor: Israel Franco, Chappaqua, NY (US)

(73) Assignee: GOGO BAND, INC., Ashland, VA (US)

( * ) Notice: Subject to any disclaimer, the term of this patent is extended or adjusted under 35 U.S.C. 154(b) by 422 days.

(21) Appl. No.: 15/485,046

(22) Filed: Apr. 11, 2017

(65) Prior Publication Data

US 2017/0290540 A1    Oct. 12, 2017

Related U.S. Application Data

(60) Provisional application No. 62/321,690, filed on Apr. 12, 2016.

(51) Int. Cl.
*A61B 5/00* (2006.01)
*A61B 5/024* (2006.01)
(Continued)

(52) U.S. Cl.
CPC ............ *A61B 5/204* (2013.01); *A61B 5/0245* (2013.01); *A61B 5/02405* (2013.01); *A61B 5/1118* (2013.01); *A61B 5/486* (2013.01); *A61B 5/742* (2013.01); *A61B 5/7405* (2013.01); *A61B 5/746* (2013.01); *A61B 5/7455* (2013.01);
(Continued)

(58) Field of Classification Search
CPC .......... A61B 8/5223; A61B 8/085; A61F 5/48
See application file for complete search history.

(56) References Cited

U.S. PATENT DOCUMENTS 6,579,247 B1 *  6/2003  Abramovitch ......... A61B 5/204
                                                  600/438
7,977,529 B2    7/2011  Bergman et al.
(Continued)

FOREIGN PATENT DOCUMENTS

JP          7255764       10/1995
JP       2005087543        4/2005
(Continued)

OTHER PUBLICATIONS

Petrican P. and Sawan, M.A. "Design of a Miniaturized Ultrasonic Bladder Volume Monitor and Subsequent Preliminary Evaluation on 41 Enuretic Patients." IEEE Transactions on Rehabilitation Engineering. vol. 6. (Year: 1998).*
(Continued)

*Primary Examiner* — Bill Thomson
*Assistant Examiner* — Amal Aly Farag
(74) *Attorney, Agent, or Firm* — Nixon Peabody LLP; Matthew T. Kitces

(57) ABSTRACT

A bedwetting monitoring method implemented by a computer, bladder monitoring device and a patient alert device and includes determining a urination volume of a bladder of a patient at which a patient will urinate, determining a trigger volume of the bladder of the patient representing a volume that is less than the urination volume, monitoring a volume of the bladder of the patient with a bladder monitoring device, and alerting the patient with the patient alert device at the trigger volume to wake the patient prior to urination.

21 Claims, 3 Drawing Sheets

(51) Int. Cl.
  *A61B 5/0245* (2006.01)
  *A61B 5/20* (2006.01)
  *A61B 8/08* (2006.01)
  *A61F 5/48* (2006.01)
  *A61B 5/11* (2006.01)

(52) U.S. Cl.
  CPC ............ *A61B 8/085* (2013.01); *A61B 8/5223* (2013.01); *A61F 5/48* (2013.01)

(56) References Cited

U.S. PATENT DOCUMENTS

| | | | |
|---|---|---|---|
| 8,648,727 B2* | 2/2014 | Caldwell | A61B 5/11 340/539.12 |
| 8,664,467 B2 | 3/2014 | Roe et al. | |
| 2003/0084906 A1* | 5/2003 | Roe | A61F 5/48 128/886 |
| 2003/0117296 A1* | 6/2003 | Seely | A61B 5/0002 340/870.07 |
| 2008/0294047 A1* | 11/2008 | Kodama | A61B 8/08 600/449 |
| 2011/0004123 A1* | 1/2011 | Companion | A61B 5/204 600/587 |
| 2012/0172783 A1* | 7/2012 | Harris | A61F 5/0013 604/20 |
| 2013/0023786 A1 | 1/2013 | Mani et al. | |
| 2014/0275849 A1* | 9/2014 | Acquista | A61B 5/0024 600/301 |
| 2016/0120455 A1* | 5/2016 | Pop | A61B 5/208 600/301 |
| 2016/0125759 A1* | 5/2016 | Dougherty | G09B 19/00 434/236 |
| 2017/0293846 A1 | 10/2017 | Zyglowicz et al. | |
| 2018/0214122 A1* | 8/2018 | Ansell | A61B 5/7267 |
| 2018/0353119 A1* | 12/2018 | Nakanishi | A61B 8/08 |

FOREIGN PATENT DOCUMENTS

| | | |
|---|---|---|
| JP | 2014079506 | 5/2014 |
| KR | 1020140141425 | 12/2014 |
| WO | 2013095231 A1 | 6/2013 |
| WO | 2017180661 | 10/2017 |

OTHER PUBLICATIONS

Niu,H., Yang,S., Liu,C., Yan,Y., Li, L., et. al, "Design of an Ultrasound Bladder Volume Measurement and Alarm System." Int. Conf. Bioinformatics and Biomedical Engineering (iCBBE), pp. 1-4 (Year: 2011).*

Kelley, C. "Evaluation of Voiding Dysfunction and Measurement of Bladder Volume." Reviews in Urology. vol. 6. Suppl. 1. pp. 32-37 (Year: 2004).*

PCT/US2017/027065, "International Search Report and Written Opinion", dated Jun. 21, 2017, 12 pages.

PCT/US2017/027065 "International Preliminary Report on Patentability" dated Oct. 25, 2018.

Canadian Office Action for CA Application No. 3020748, dated Aug. 15, 2019.

European Supplementary Search Report for EP Application No. 17783007.2, dated Oct. 24, 2019.

Office Action for U.S. Appl. No. 15/485,057, dated Feb. 11, 2020.

Mika Tarvainen Ph.D, Kubios HRV, User's Guide, Jul. 6, 2012, pp. 1-44, Biosignal Analysis and Medical Group (BSAMIG), Department of Applied Physics University of Eastern Finland, Kuopio, Finland Imaging.

* cited by examiner

BEDWETTING TRAINING DEVICE AND METHOD

CROSS REFERENCE TO RELATED APPLICATIONS

The present application claims priority to U.S. Patent Application No. 62/321,690, filed Apr. 12, 2016, entitled "BEDWETTING TRAINING DEVICE AND METHOD," the entirety of which is hereby incorporated by reference.

FIELD OF THE INVENTION

The present application relates to a bedwetting conditional training device and method, and more specifically, the present invention relates to a bedwetting training device and method for providing therapy and training for bed wetting patients.

BACKGROUND

Presently, bedwetting, also known as nighttime incontinence or nocturnal enuresis, is a problem that affects up to 17% of children 6 years of age and 1% of adults. Bedwetting is described as the involuntary loss of urinary control while sleeping. It can be associated with excessive urine production, but the hallmark of the disease is that the patient is unable to recognize that the bladder is full and therefore is unable to suppress the ensuing bladder contraction. Inappropriate recognition of bladder signals in the brain lead to bedwetting which is in contrast to nocturia, when the patient awakes to void either due to large amounts of urine of the need to void but no accidents ensue. Bedwetting may be treated through various therapeutic methods which include medications, bedwetting alarms (mediated through electrical conductance, e.g., a circuit is completed when the urine which acts as a conductor between two electrodes attached to the clothes or a mattress pad), hypnotherapy and other conditioning.

Conventional alarm therapy commonly utilizes the salt in urine to complete the circuit between two electrodes attached to the clothes or a mattress pad, triggering an alarm when the patient wets themselves. While such conventional measures are effective in 50 to 70% of the patients, the fundamental drawback is that the person is awoken only after they wet themselves. As such, there is no stimulation or conditioning that occurs while the bladder is filling and, instead, the person is only notified after the event occurs. Waking the child after the fact becomes a form of treatment dependent on negative reinforcement. The present invention was developed in light of these and other issues.

SUMMARY

A bedwetting monitoring method implemented by a computer, bladder monitoring device and a patient alert device and includes determining a urination volume of a bladder of a patient at which a patient will urinate, determining a trigger volume of the bladder of the patient representing a volume that is less than the urination volume, monitoring a volume of the bladder of the patient with a bladder monitoring device, and alerting the patient with the patient alert device at the trigger volume to wake the patient prior to urination.

DETAILED DESCRIPTION

Figure 1:
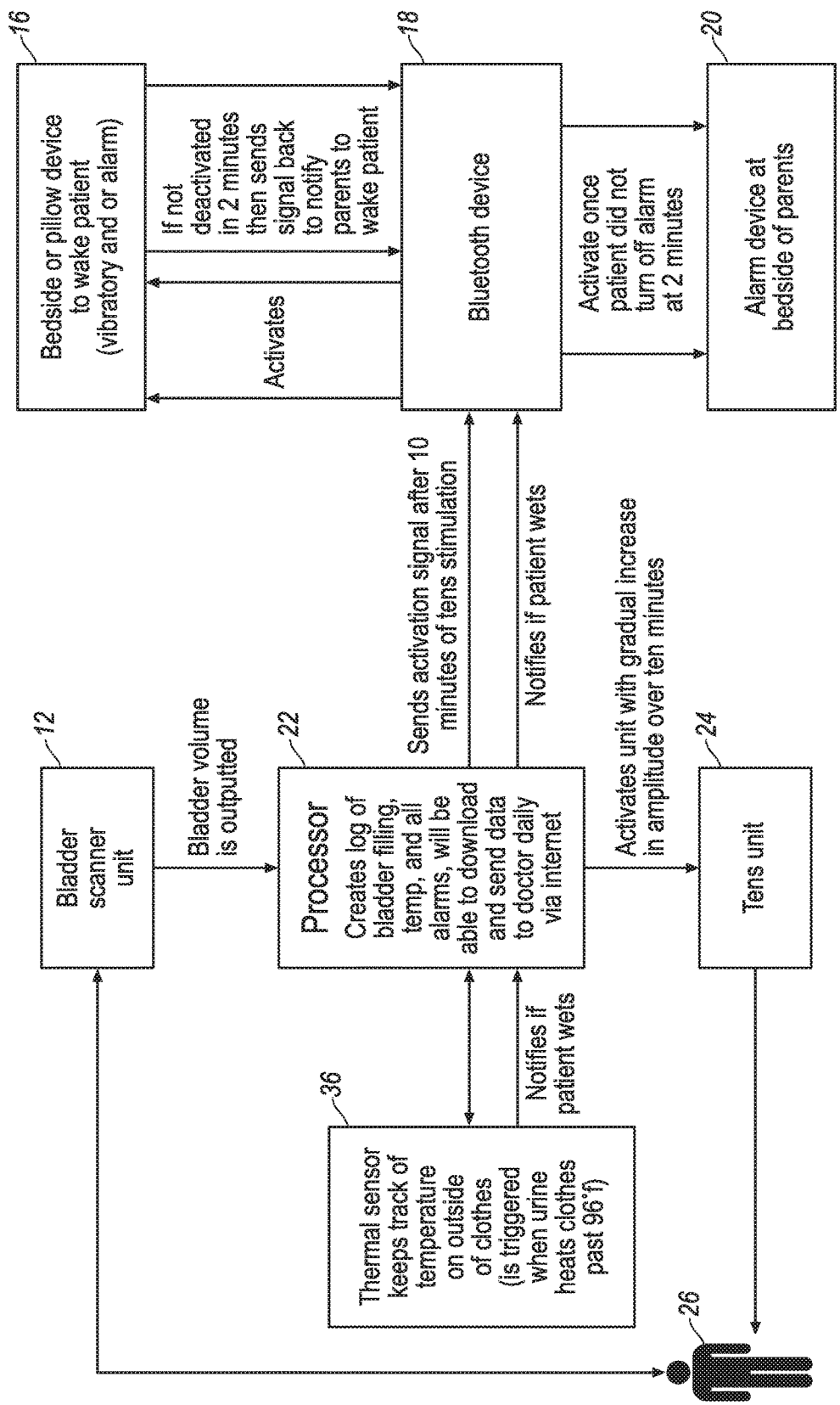
FIG. 1 is a schematic view of a bedwetting training device and method according to one aspect of the invention.

Referring now to FIG. 1, an embodiment of a bedwetting training device and method according to one aspect of the present invention is shown and described. In FIG. 1, the bedwetting training device 10 includes a processor or computer 22 connected to a bladder scanner unit 12 which, in turn, is connected to either an alarm (e.g., bell, siren or other noise making device), vibration device (e.g., under the pillow, chest strap, or any other body part where a device capable of generating a vibration can be applied) or a transcutaneous electrical nerve stimulation (TENS) unit 24. The bladder scanner unit 12 may be an ultrasound, photo-optical or electrocardiogram (EKG) device or other known technique of scanning the internal organs or workings of a person or animal to determine a level of urine in the bladder of such person or animal. The photooptical or EKG device capable of measuring heart rate variability, which is the variability between RR intervals (e.g., the time period between the peaks of successive QRS complexes) or between heart beats, could use electrical current generated from the heart or pulsations picked up with a photo optical or infrared scanning device on the skin or any such device capable of recording the RR interval between heart beats. Alternatively, the bladder scanner unit 12 may instead be a different technique of determining when a bladder reaches a certain volume.

The computer 22 includes a processor, memory, ports and other features. The computer may alternately be a mobile device such as a mobile phone (e.g., smartphone) or any other device capable of processing and computing the data described herein. A patient alert system or a TENS unit 24, (or in some cases a neuromuscular electrical stimulation (NMES) unit or any other stimulation technique, vibration technique, audible or visual alarm or other suitable system for stimulating a patient), is, in one embodiment, an electrical stimulation unit that provides electrical current at a particular frequency, amperage, voltage or intensity to a patient. However, in one aspect, the TENS unit 24 is applied to the parasacral area with two conductive patches, one on each side of the spine just at the level of the s2-3 foramen. The computer 22 is responsive to input from the bladder scanner unit 12 to store volumes sensed by the bladder scanner unit or output signals. Once a preset threshold to trigger the TENS unit 24 is achieved, the TENS is activated.

A Bluetooth device 18 receives signals to and from the computer 22 to activate additional alarms such as alarm 16 and alternate alarm 20. Alarm 16 may be an audio or visual alarm located in the bedroom of the patient or person that sounds or lights in response to a wetting event (e.g., when a patient wets the bed during sleep). Likewise, alternate alarm 20 may be an additional alarm located in, for example, the bedroom of a parent of a child or caregiver to whom treatment is being provided.

The computer 22 is responsive to the bedwetting sensor (e.g., bedwetting sensor 14 of FIG. 2), which may be a thermal or moisture sensor positioned on the patient's clothes or under the patient, to actuate either the alarm 16 or the alternate alarm 20 upon a wetting event occurrence. As will be described further, the bedwetting sensor (e.g., bedwetting sensor 14 of FIG. 2) may also be used to update data such as trigger volume that will be described.

Figure 2:
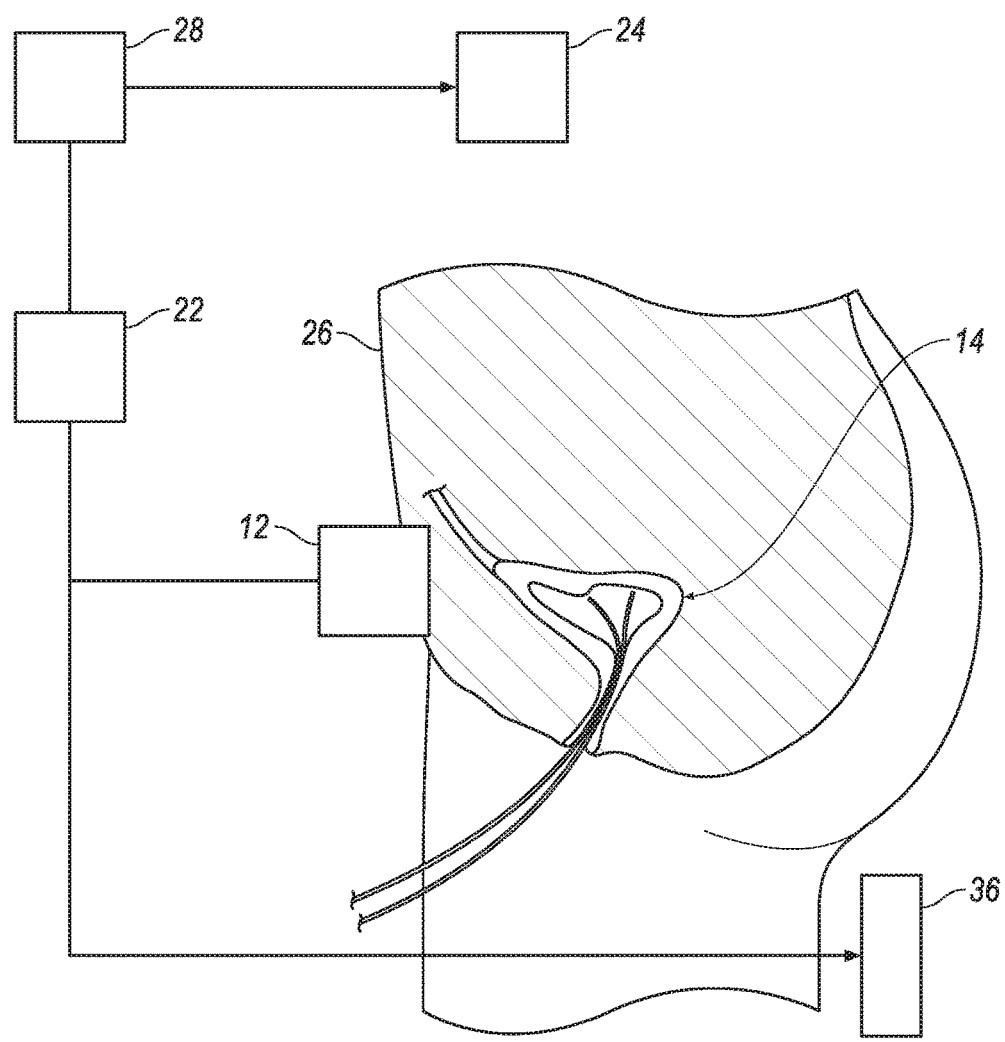
FIG. 2 is a schematic view of a bedwetting training device and method according to another aspect of the invention.

Referring to FIG. 2, bladder scanner unit 12 is shown positioned on a patient 26 and connected to the computer 22. The bladder scanner unit 12 is applied to an area of the patient sufficient to measure and sense the volume in the bladder (e.g., suprapubic area). Alternatively, if the bladder scanner unit uses other techniques to sense bladder fill, such as a heart rate monitor tracking heart rate, it may be attached as required (e.g., on the anterior chest wall to sense cardiac signals). A controller 28 is connected to the computer 22 and responsive thereto to instruct the alarm (e.g., bell, siren or other noise making device), vibration device (e.g., under the pillow, chest strap, or any other body part where a device capable of generating a vibration can be applied), or a TENS unit 24 are other patient alert system to actuate.

The operation of one aspect of the present invention will now be described. In one aspect, the system of the present invention is first calibrated for a particular patient 26. The process starts where the initial conditions of bedwetting are obtained through a calculation based on weight. The calibration process then proceeds by the patient wearing the device for several days to obtain the volume at which the patient routinely wets the bed. This information is stored and processed to obtain an average volume at wetting.

In step 42, to obtain the initial conditions at the start of the several day period, the weight of the patient 26 is obtained. The weight is used to calculate an amount of urine that is generated per hour. In one aspect, the amount of urine generated per hour is equal to the Wt(kg)×2 ml=urine output (e.g., urine generated by the body) per hour in ml. This total is then be multiplied by 0.1666 to obtain the output in 10 minute intervals. Accordingly, for example, a 40 kg patient multiplied by 2 which equals 80 ml in 1 hour or, per 10 min, equals=16.66%*80=13 ml. From this calculation, the amount of expected urine output per time can be calculated and therefore the amount of time may be calculated when the patient will likely urinate.

In step 46, the system described in FIGS. 1 and 2 is attached to patient 26 each night for approximately a week. Here, TENS unit 24 is attached to the patient 26. Likewise, bedwetting sensor 36 is positioned on or under the patient to sense moisture or temperature to actuate in response to bed wetting by the patient 26. Other items such as the computer 22 and bladder scanner unit 12 are connected to the patient 26 to sense bladder fill. The system monitors urine output via the ultrasound (or other) device and in real-time makes an estimate of urine output (e.g., the amount of urine generated by the body) per hour as well. If an EKG/heart rate variability monitor is utilized the change in the heart rate variability at various frequencies as determined by Fourier transformations or other signal processing methods and are used to determine the change in the autonomic tone of the patient which is directly associated with bladder filling. These signal changes can be in the ultralow, very low, low, and high frequency ranges according to software developed by Kubios to run Fourier analysis on the RR interval.

Utilizing the average volume determined from the prior night's use of the device over the period of the week, a threshold volume will be set at 10 ml below the average volume when wetting occurs (e.g., 10 ml below the average urination volume). Based on urine output calculations either via the bladder ultrasound or the manual weight based calculation (which can be used as a backup if the bladder ultrasound is not properly receiving signals), the TENS unit will be set to be activated at a trigger volume and trigger time which is 10 minutes prior to the threshold volume. Thus, the amount of urine output rate is then calculated by multiplying by 0.1666 to give the 10 minute fill rate. The processor then calculates the expected time to reach the trigger volume referred to as the trigger time. At the trigger time the TENS unit is activated.

Figures 3, 4:
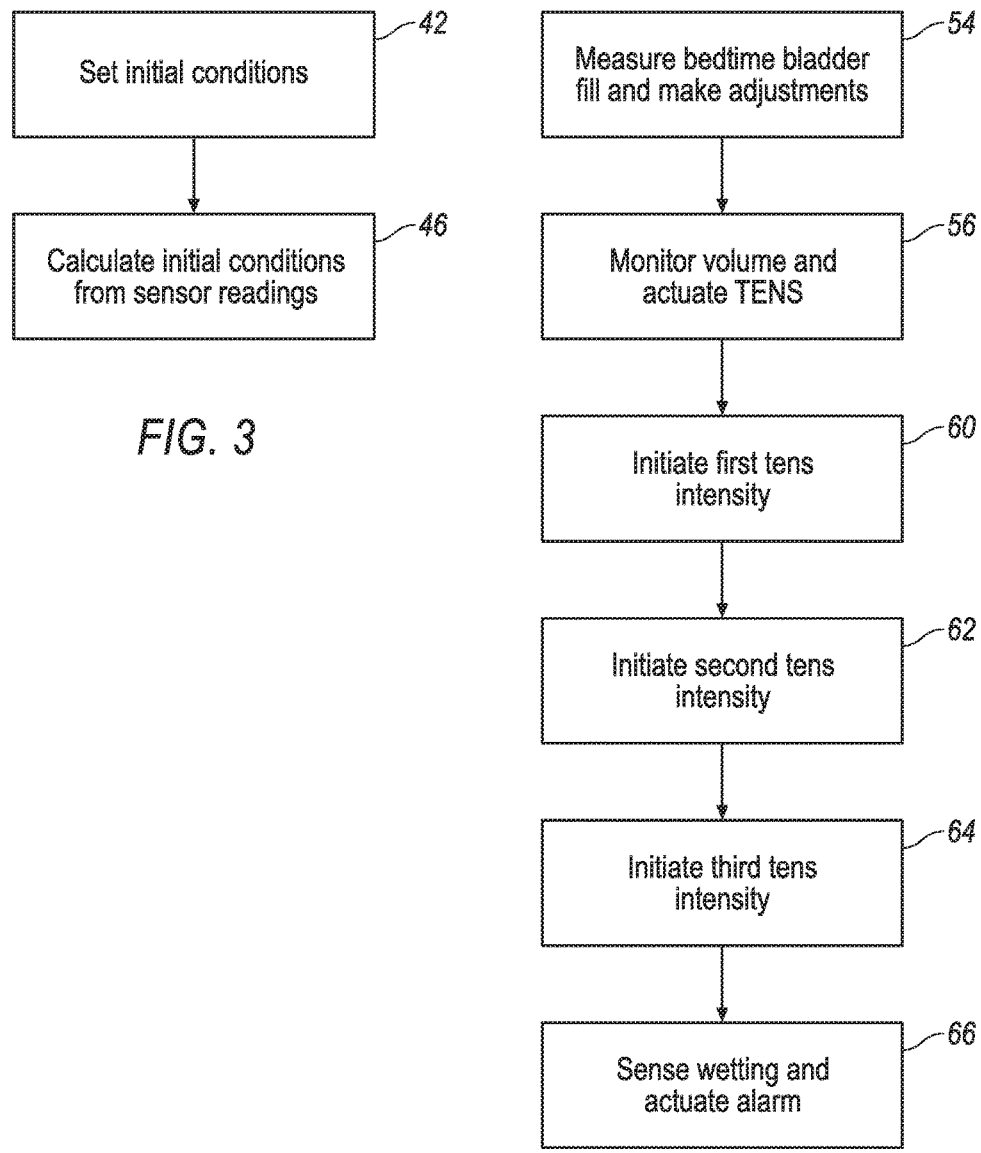
FIG. 3 is a diagrammatical view of a bedwetting training device and method according to another aspect of the invention.
FIG. 4 is a diagrammatical view of a bedwetting training device and method according to another aspect of the invention.

The process described in FIG. 4 is then used to provide therapy to the patient. First, in step 54, before the patient goes to sleep, bladder scanner unit 12 obtains the pre-void volume as well as the post void urine volume in the bladder. The post void volume is the amount of urine remaining in the bladder when the person goes to sleep. This post void urine volume is subtracted from the threshold urination volume that was obtained previously. From this, a change in volume required to cause urination is determined. For example, if the urination volume is 100 cc and the post-void urination volume is 20 cc, then a delta volume of 80 cc is required to cause urination during sleep. This calculation is done each time the patient 26 goes to sleep. This will allow for the calculation of an estimated time that wetting may occur and used to calculate trigger volume and trigger time. This information can be transmitted to the parents and the child for their knowledge. This calculation is also used as a failsafe if the bladder scanner fails to record volume due to positional changes or excessive gas that obscures the proper measurement of the bladder volume. It is possible that patients with post void urination volumes of excess of 20 ml may have other voiding issues and this will be used to inform the clinician of the need for additional therapy.

In step 56 the bladder volume is measured by bladder scanner unit 12 during sleep. Bladder scanner unit 12 provides the data obtained through the scan to computer 22. The information may be fed through a serial port or universal serial bus (USB) connector in any particular format that is thereafter interpreted by the computer 22 into a usable format. Alternatively, bladder scanner unit may be a timer that measures the urine output via the equation provided above. The computer 22 processes the data received to identify volume information of the bladder per unit time. Computer 22 identifies the initial volume and uses the trigger volume and trigger time to begin actuation of the TENS unit 24 for which wetting is likely to occur. This trigger volume may be the estimate as provided in FIG. 3 and updated after the steps of FIG. 4 are repeated.

At the trigger volume and trigger time at step 60, computer 22 actuates microcontroller 28 to initiate the patient alert system of either and alarm (e.g., bell, siren or other noise making device), vibration device (e.g., under the pillow, chest strap, or any other body part where a device capable of generating a vibration can be applied) or a TENS unit 24 to send a predefined signal (e.g., a predefined combination of voltage, frequency and/or current) to the patient 26 to stimulate the patient 26. The signal is at a relatively lower intensity level relative to the signal sent in response to the urination volume to begin stimulation of the patient 26 before the threshold volume is achieved.

In step 62, a second tens intensity is initiated that is larger than the first tens intensity. This may occur sometime after the first tens stimulation but before the threshold volume is achieved. In one example, every 2 minutes from the trigger time, the processor will instruct the TENS unit to increase the intensity incrementally by 20% until an upper threshold intensity is achieved. For example, step 64 initiates a third intensity. In this example, after 30 seconds, or any other suitable value, at step 66 at the highest intensity, the alarm will be set off for the patient and the parents, prior to wetting, for example at the threshold volume. It will be understood that additional steps beyond step 64 may be employed for increases in intensities. For example, different trigger volumes and trigger times from that described herein may be used and multiple and different trigger times may be employed such that different intensities and different alarms occur at different times.

If wetting occurs, wetting sensor 36 reads the event through sensing moisture or temperature and sends a signal to the computer 22 indicating that wetting has occurred and measures the volume at which this happens. In response the signal from wetting sensor 36, computer 22 records the volume when wetting is sensed. This volume is recorded and if it varies significantly from the original calculated volumes it will be used to calculate the threshold volume, trigger volume and trigger time. For example, if urination occurred at volume of 150 cc, 10 cc may be subtracted to result in a volume of 140 cc, and an additional 10 minutes subtracted by computer 22 to set the new trigger volume and trigger time. Thus, once the bladder reaches 10 minutes before 140 cc is reached, computer 22 determines that the trigger volume has been reached and will actuate the TENS unit 24. It will be noted that although the trigger time is calculated by subtracting 10 minutes from the threshold volume and all the threshold volume is calculated at 10 cc less than the volume at which urination occurs, all these variables may be changed and altered. For example, the trigger volume may be set at the actual volume at which urination occurs. The trigger volume may be set at 10 cc less than when urination actually occurs. Or, the trigger volume and time may be set at some different or arbitrary value when the threshold volume is determined. Many different configurations and values may be employed to accomplish stimulating a patient at a point prior to urination.

In this specification, various preferred embodiments may have been described with reference to the accompanying drawings. It will, however, be evident that various modifications and changes may be made thereto, and additional embodiments may be implemented, without departing from the broader scope of the invention as set forth in the claims that follow. The present invention is thus not to be interpreted as being limited to particular embodiments and the specification and drawings are to be regarded in an illustrative rather than restrictive sense.

It will be appreciated that the system and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

As used below, any reference to a series of examples is to be understood as a reference to each of those examples disjunctively (e.g., "Examples 1-4" is to be understood as "Examples 1, 2, 3, or 4").

Example 1 is a bedwetting monitoring method implemented by a computer, bladder monitoring device and a patient alert device, comprising: determining urination volume of a bladder of a patient at which a patient will urinate; determining a trigger volume of the bladder of the patient representing a volume that is less than the urination volume when the patient should be stimulated prior to urination; monitoring a volume of the bladder of the patient with a bladder monitoring device; and alerting the patient with the patient alert device at the trigger volume to wake the patient prior to urination.

Example 2 is the bedwetting monitoring method according to example 1, further comprising: alerting the patient with the patient alert device at a first intensity when the trigger volume is reached; and increasing the intensity of the patient alert device after the trigger volume has been reached to increase stimulation of the patient prior to the urination volume being reached.

Example 3 is the bedwetting monitoring method according to examples 1 or 2, wherein the bladder monitoring device comprises an ultrasound or photo optical sensor that measures the volume of the bladder.

Example 4 is the bedwetting monitoring method according to examples 1-3, wherein the urination volume of the bladder is calculated with an EKG that measures heart rate variability upon the EKG sensing heart rhythms associated with urination.

Example 5 is the bedwetting monitoring method according to examples 1-4, wherein the bladder monitoring device is done by the computer as a calculation that calculates an amount of urine generated in the bladder per unit time.

Example 6 is the bedwetting monitoring method according to examples 1-5, further comprising a bedwetting sensor that provides a signal representative of whether the patient wets the bed.

Example 7 is the bedwetting monitoring method according to example 6, further comprising setting the urination volume and trigger volume based on the signal from the bedwetting sensor.

Example 8 is the bedwetting monitoring method according to example 7, further comprising alerting the patient with the patient alert device when the signal from the bedwetting sensor is provided.

Example 9 is the bedwetting monitoring method according to examples 1-8, wherein the patient alert device is a TENS, NMES, audible, vibration or visual alarm.

Example 10 is a bedwetting monitoring device, comprising: a computer; a bladder monitoring device connected to the computer; a patient alert device connected to the computer; wherein: the computer determines a urination volume of a bladder of a patient at which a patient will urinate; the computer determines a trigger volume of the bladder of the patient representing a volume that is less than the urination volume; the computer stores the trigger volume and the urination volume in a memory device; the bladder monitoring device monitors a volume of the bladder of the patient; the patient alert device alerts the patient at the trigger volume to wake the patient prior to urination.

Example 11 is the bedwetting monitoring device according to example 10, further comprising: alerting the patient with the patient alert device at a first intensity when the trigger volume is reached; and increasing the intensity of the patient alert device after the trigger volume has been reached.

Example 12 is the bedwetting monitoring device according to examples 10 or 11, wherein the bladder monitoring device comprises an ultrasound or photo optical sensor that measures the volume of the bladder.

Example 13 is the bedwetting monitoring device according to examples 10-12, wherein the urination volume of the bladder is calculated with an EKG that measures heart rate variability.

Example 14 is the bedwetting monitoring device according to examples 10-13, further comprising a bedwetting sensor that provides a signal representative of whether the patient wets the bed.

Example 15 is the bedwetting monitoring device according to example 14, wherein the computer sets the urination volume and trigger volume based on the signal from the bedwetting sensor.

Example 16 is the bedwetting monitoring device according to examples 10-15, wherein the patient alert device is a TENS, NMES, audible, vibration or visual alarm.

The invention claimed is:

1. A bedwetting training method implemented by a computer, bladder monitoring device, and a patient alert device, the method comprising:
determining a urination volume of a bladder of a patient at which the patient will urinate;
determining a trigger volume of the bladder of the patient representing a volume that is less than the urination volume when the patient should be stimulated prior to urination;
monitoring a volume of the bladder of the patient with a bladder monitoring device, wherein monitoring the volume of the bladder comprises:
measuring heart rate variability of the patient;
detecting signal changes of the heart rate variability at various frequencies, wherein detecting signal changes at the various frequencies comprises detecting signal changes in a plurality of frequency ranges including a very low frequency band, a low frequency band, and a high frequency band;
determining bladder filling based on the detected signal changes; and
estimating the volume of the bladder based on the determined bladder filling; and
alerting the patient with the patient alert device at the trigger volume to wake the patient prior to urination.

2. The bedwetting training method according to claim 1, further comprising:
alerting the patient with the patient alert device at a first intensity when the trigger volume is reached; and
increasing the intensity of the patient alert device after the trigger volume has been reached to increase stimulation of the patient prior to the urination volume being reached.

3. The bedwetting training method according to claim 1, wherein the bladder monitoring device comprises an ultrasound or photo optical sensor, and wherein the volume of the bladder is calculated using the ultrasound or the photo optical sensor.

4. The bedwetting training method according to claim 1, wherein the heart rate variability is determined using a photo optical sensor sensing heart rhythms associated with urination.

5. The bedwetting training method according to claim 1, wherein determining the volume of the bladder based on the detected signal changes comprises:
determining an initial volume of the bladder at a first time;
calculating an amount of urine generated in the bladder per unit time based on the detected signal changes;
determining an amount of elapsed time since the first time
multiplying the amount of urine generated per unit time by the amount of elapsed time to determine the volume of the bladder.

6. The bedwetting training method according to claim 1, further comprising a bedwetting sensor that provides a signal representative of whether the patient wets the bed.

7. The bedwetting training method according to claim 6, further comprising setting the urination volume and trigger volume based on the signal from the bedwetting sensor.

8. The bedwetting training method according to claim 7, further comprising alerting the patient with the patient alert device when the signal from the bedwetting sensor is provided.

9. The bedwetting training method according to claim 1, wherein the patient alert device is a transcutaneous electrical nerve stimulation (TENS), neuromuscular electrical stimulation (LAMES), audible, vibration, or visual alarm.

10. The bedwetting training method according to claim 1, wherein the plurality of frequency ranges further includes an ultralow low frequency band.

11. A bedwetting training device, comprising:
a computer;
a bladder monitoring device connected to the computer; and
a patient alert device connected to the computer;
wherein:
the computer determines a urination volume of a bladder of a patient at which the patient will urinate;
the computer determines a trigger volume of the bladder of the patient representing a volume that is less than the urination volume;
the computer stores the trigger volume and the urination volume in a memory device;
the bladder monitoring device monitors a volume of the bladder of the patient, wherein the bladder monitoring device:
measures heart rate variability of the patient;
detects signal changes of the heart rate variability at various frequencies, wherein detecting signal changes at the various frequencies comprises detecting signal changes in a plurality of frequency ranges including a very low frequency band, a low frequency band, and a high frequency band;
determines bladder filling based on the detected signal changes; and estimates the volume of the bladder based on the determined bladder filling; and the patient alert device alerts the patient at the trigger volume to wake the patient prior to urination.

12. The bedwetting training device according to claim 11, further comprising:

alerting the patient with the patient alert device at a first intensity when the trigger volume is reached; and increasing the intensity of the patient alert device after the trigger volume has been reached.

13. The bedwetting training device according to claim 11, wherein the bladder monitoring device comprises an ultrasound or photo optical sensor, and wherein the volume of the bladder is calculated using the ultrasound or the photo optical sensor.

14. The bedwetting training device according to claim 11, wherein the bladder monitoring device comprises a photo optical sensor that measures the heart rate variability.

15. The bedwetting training device according to claim 11, further comprising a bedwetting sensor that provides a signal representative of whether the patient wets the bed.

16. The bedwetting training device according to claim 15, wherein the computer sets the urination volume and trigger volume based on the signal from the bedwetting sensor.

17. The bedwetting training device according to claim 11, wherein the patient alert device is a transcutaneous electrical nerve stimulation (TENS), neuromuscular electrical stimulation (LAMES), audible, vibration, or visual alarm.

18. The bedwetting training device according to claim 11, wherein the bladder monitoring device is further configured to:

determine an initial volume of the bladder at a first time;

calculate an amount of urine generated in the bladder per unit time based on the detected signal changes;

determine an amount of elapsed time since the first time; and multiply the amount of urine generated per unit time by the amount of elapsed time to determine the volume of the bladder.

19. The bedwetting training method according to claim 1, wherein the heart rate variability is determined using a photo optical sensing device.

20. The bedwetting training device according to claim 11, wherein the bladder monitoring device comprises a photo optical sensor that measures the heart rate variability.

21. The bedwetting training device according to claim 11, wherein the plurality of frequency ranges further includes an ultralow low frequency band.

* * * * *